US00PP21338P2

(12) United States Plant Patent
Dümmen

(10) Patent No.: US PP21,338 P2
(45) Date of Patent: Sep. 28, 2010

(54) ***BEGONIA* PLANT NAMED 'BBSWEET'**

(50) Latin Name: *Begonia×hiemalis*
Varietal Denomination: BBSWEET

(75) Inventor: Tobias Gunter Dümmen, Rheinberg (DE)

(73) Assignee: Begonia Breeders Association B.V., Rijsenhout (NL)

( * ) Notice: Subject to any disclaimer, the term of this patent is extended or adjusted under 35 U.S.C. 154(b) by 0 days.

(21) Appl. No.: 12/386,662

(22) Filed: Apr. 20, 2009

(51) Int. Cl.
*A01H 5/00* (2006.01)

(52) U.S. Cl. ..... Plt./348

(58) Field of Classification Search ..... Plt./348
See application file for complete search history.

*Primary Examiner*—Annette H Para
(74) *Attorney, Agent, or Firm*—C. A. Whealy

(57) ABSTRACT

A new and distinct cultivar of *Begonia* plant named 'BBSWEET', characterized by its upright and mounded plant habit; freely branching habit; numerous fragrant double flowers that are dark pink in color; and good postproduction longevity.

1 Drawing Sheet

Botanical designation: *Begonia×hiemalis.*

Cultivar denomination: 'BBSWEET'.

BACKGROUND OF THE INVENTION

The present invention relates to a new and distinct cultivar of *Begonia* plant, botanically known as *Begonia×hiemalis,* commercially known as Elatior *Begonia,* and hereinafter referred to by the name 'BBSWEET'.

The new *Begonia* plant is a product of a planned breeding program conducted by the Inventor in Rijsenhout, The Netherlands. The objective of the breeding program is to develop new freely branching *Begonia* cultivars with attractive flower color and fragrance.

The new *Begonia* plant originated from a cross-pollination made by the Inventor in December, 2005 of two unnamed proprietary selections of *Begonia×hiemalis,* not patented. The new *Begonia* was discovered and selected by the Inventor as a single flowering plant from within the progeny of the stated cross-pollination in a controlled greenhouse environment in Rijsenhout, The Netherlands in May, 2006.

Asexual reproduction of the new *Begonia* plant by terminal cuttings in a controlled greenhouse environment in Rijsenhout, the Netherlands since the autumn of 2006, has shown that the unique features of this new *Begonia* plant are stable and reproduced true to type in successive generations.

SUMMARY OF THE INVENTION

Plants of the new *Begonia* have not been observed under all possible environmental conditions. The phenotype may vary somewhat with variations in environment such as temperature and light intensity, without, however, any variance in genotype.

The following traits have been repeatedly observed and are determined to be the unique characteristics of 'BBSWEET'. These characteristics in combination distinguish 'BBSWEET' as a new and distinct cultivar of *Begonia:*

1. Upright and mounded plant habit.
2. Freely branching habit.

3. Numerous fragrant double flowers that are dark pink in color.
4. Good postproduction longevity.

Plants of the new *Begonia* differ primarily from plants of the parent selections primarily in fragrance as plants of the parent selections are not fragrant. In addition, plants of the male parent selection have single flowers.

Plants of the new *Begonia* can also be compared to plants of *Begonia×hiemalis* 'BBBON', disclosed in U.S. Plant Pat. No. 18,587. In side-by-side comparisons conducted in Rijsenhout, The Netherlands, plants of the new *Begonia* differed from plants of 'BBBON' in the following characteristics:

1. Plants of the new *Begonia* had fewer tepals per flower than plants of 'BBBON'.
2. Plants of the new *Begonia* and 'BBBON' differed in flower color as plants of 'BBBON' had lighter pink-colored flowers.
3. Plants of the new *Begonia* were fragrant whereas plants of 'BBBON' were not fragrant.

BRIEF DESCRIPTION OF THE PHOTOGRAPH

The accompanying colored photograph illustrates the overall appearance of the new *Begonia*, showing the colors as true as it is reasonably possible to obtain in colored reproductions of this type. Colors in the photograph may differ slightly from the color values cited in the detailed botanical description which accurately describe the colors of the new *Begonia.* The photograph comprises a side perspective view of a typical flowering plant of 'BBSWEET' grown in a container.

DETAILED BOTANICAL DESCRIPTION

Plants used for the aforementioned photograph and following observations and measurements were grown in Rijsenhout, The Netherlands in 13-cm containers and under commercial practice in a glass-covered greenhouse during the spring and summer. During the production of the plants, day and night temperatures ranged from 15° C. to 20° C. and light levels were about 18,000 lux. Plants used for the photograph and the description were 15 weeks old. In the following description, color references are made to The Royal Horticultural Society Colour Chart, 2001 Edition, except where general terms of ordinary dictionary significance are used.

Botanical classification: *Begonia×hiemalis* 'BBSWEET'.

Commerical classification: Elatior *Begonia.*

Parentage:

*Female, or seed, parent.*—Unnamed proprietary selection of *Begonia×hiemalis,* not patented.

*Male, or pollen, parent.*—Unnamed proprietary selection of *Begonia×hiemalis,* not patented.

Propagation:

*Type.*—By terminal vegetative cuttings.

*Time to initiate roots.*—About 15 days at temperatures of about 20° C.

*Time to produce a rooted young plant.*—About 14 to 18 days at temperatures of about 20° C.

*Root description.*—Medium in thickness, fibrous, white in color; plants of the new *Begonia* have not been observed to form tubers.

*Rooting habit.*—Freely branching; moderately dense.

Plant description:

*Plant form.*—Compact, upright and mounded plant habit, inverted triangle; freely branching with good stem and stem base strength. Flowers are double and abundant. Moderately vigorous growth habit.

*Plant height.*—About 20 cm to 25 cm.

*Plant width.*—About 25 cm to 30 cm.

*Basal branch description.*—Quantity: Freely basal branching with about five to six basal branches developing per plant. Length: About 10 cm to 15 cm. Diameter: About 1 cm to 3 cm. Texture: Smooth, glabrous. Color: Close to 144B.

*Leaf description.*—Arrangement: Simple, alternate. Length: About 8 cm to 10 cm. Width: About 5 cm to 6 cm. Shape: Deltoid to ovate. Apex: Acuminate. Base: Cordate. Margin: Serrate. Texture, upper and lower surfaces: Smooth, glabrous; velvety. Venation pattern: Palmate. Color: Developing and fully expanded leaves, upper surface: Close to 137A; venation, close to 141C. Developing and fully expanded leaves, lower surface: Close to 137B; venation, close to 141C. Petiole length: About 4 cm to 6 cm. Petiole diameter: About 4 mm. Petiole texture, upper and lower surfaces: Smooth, glabrous. Petiole color, upper and lower surfaces: Close to 138B.

Flower description:

*Flowering habit.*—Double flowers with numerous tepals arranged in axillary cymes; typically four to five open flowers per cyme; many cymes in flower simultaneously; flowers positioned upright and outwardly above the foliage.

*Fragrance.*—Present; sweet, pleasant.

*Natural flowering season.*—Plants will flower continuously year round in the greenhouse, however plants flower earlier and more abundantly during the summer in The Netherlands.

*Postproduction longevity.*—Good postproduction longevity, flowers last about four weeks on the plant; flowers persistent.

*Cyme height.*—About 4 cm to 5 cm.

*Cyme diameter.*—About 6 cm to 7 cm.

*Flowers.*—Shape: Oval; rose-like. Diameter: About 4 cm to 6 cm. Depth (height): About 1 cm to 2 cm.

*Flower buds.*—Shape: Elliptic. Length: About 1 cm to 2 cm. Diameter: About 1 cm to 2 cm.

*Tepals.*—Arrangement: Rosette. Quantity per flower: Usually about six to eight per flower. Length: About 2 cm to 3 cm. Width: About 2 cm to 3 cm. Shape: Obovate. Apex: Rounded, obtuse. Base: Cordate. Margin: Entire; undulate. Texture, upper and lower surfaces: Smooth, glabrous; satiny. Color: When opening, upper and lower surfaces: Close to 52A; color does not fade with development. Fully opened, upper and lower surfaces: Close to 52A.

*Flower bracts.*—Quantity/arrangement: Two, opposite. Shape: Broadly ovate. Apex: Acute. Margin: Entire. Texture, upper and lower surfaces: Smooth, glabrous. Color, upper surface: Close to 144D; at the margins, close to 52D. Color, lower surface: Close to 145B; at the margins, close to 52D.

*Peduncles.*—Angle: Erect to about 30° to 45° from vertical. Length: About 4 cm to 5 cm. Diameter: About 3 mm to 4 mm. Texture: Smooth, glabrous. Color: Close to 144B.

*Pedicels.*—Angle: About 30° to 45° from the peduncle. Length: About 2 cm to 3 cm. Diameter: About 2 mm to 3 mm. Texture: Smooth, glabrous. Color: Close to 146A.

*Reproductive organs.*—Stamens: None observed. Pistils: None observed.

*Seed/fruit.*—Seed and fruit production have not been observed.

Disease/pest resistance: Resistance to pathogens and pests common to *Begonia* has not been observed.

Temperature tolerance: Plants of the new *Begonia* have been observed to tolerate temperatures from about 10° C. to about 35° C.

It is claimed:

1. A new and distinct *Begonia* plant named 'BBSWEET' as illustrated and described.

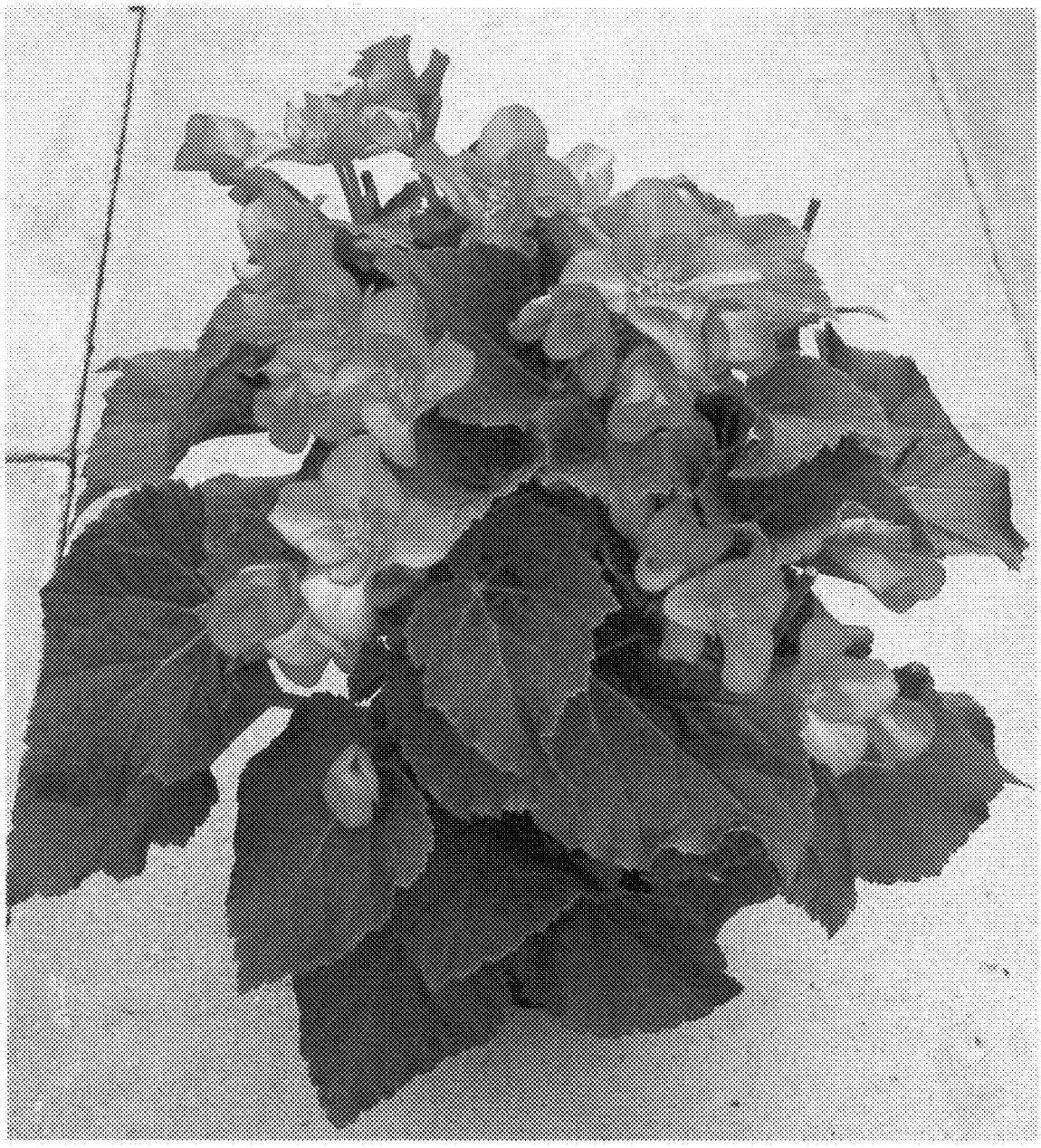

* * * * *